United States Patent
Kokones et al.

(10) Patent No.: US 8,260,425 B2
(45) Date of Patent: Sep. 4, 2012

(54) DEEP BRAIN STIMULATION SYSTEM WITH INPUTS

(75) Inventors: Scott Kokones, Cleveland, OH (US); Keith Carlton, Cleveland, OH (US); Alan Greszler, Bay Village, OH (US)

(73) Assignee: Intelect Medical, Inc., Cleveland, OH (US)

( * ) Notice: Subject to any disclaimer, the term of this patent is extended or adjusted under 35 U.S.C. 154(b) by 17 days.

(21) Appl. No.: 11/871,468

(22) Filed: Oct. 12, 2007

(65) Prior Publication Data

US 2009/0099624 A1  Apr. 16, 2009

(51) Int. Cl.
*A61N 1/36* (2006.01)

(52) U.S. Cl. .......................................... 607/45
(58) Field of Classification Search .................. 607/45
See application file for complete search history.

(56) References Cited

U.S. PATENT DOCUMENTS

| | | | |
|---|---|---|---|
| 5,293,879 A * | 3/1994 | Vonk et al. ............... | 600/595 |
| 5,749,904 A | 5/1998 | Gliner et al. | |
| 6,227,203 B1 * | 5/2001 | Rise et al. ............... | 128/898 |
| 6,442,432 B2 | 8/2002 | Lee | |
| 6,507,759 B1 | 1/2003 | Prutchi et al. | |
| 6,609,031 B1 | 8/2003 | Law et al. | |
| 6,631,297 B1 | 10/2003 | Mo | |
| 6,654,642 B2 | 11/2003 | North et al. | |
| 6,662,053 B2 | 12/2003 | Borkan | |
| 6,684,106 B2 | 1/2004 | Herbst | |
| 6,690,974 B2 | 2/2004 | Archer et al. | |
| 6,748,276 B1 | 6/2004 | Daignault, Jr. et al. | |
| 6,819,956 B2 * | 11/2004 | DiLorenzo ............... | 607/45 |
| 6,937,891 B2 | 8/2005 | Leinders et al. | |
| 6,944,501 B1 | 9/2005 | Pless | |
| 7,127,297 B2 | 10/2006 | Law et al. | |
| 7,228,179 B2 | 6/2007 | Campen et al. | |
| 7,254,445 B2 | 8/2007 | Law et al. | |
| 7,266,412 B2 | 9/2007 | Stypulkowski | |
| 2004/0138518 A1 | 7/2004 | Rise et al. | |
| 2005/0131482 A1 * | 6/2005 | Mattes et al. ............... | 607/36 |
| 2006/0224187 A1 * | 10/2006 | Bradley et al. ............... | 607/2 |
| 2007/0129774 A1 | 6/2007 | Bourget et al. | |
| 2007/0179558 A1 * | 8/2007 | Gliner et al. ............... | 607/45 |
| 2007/0225674 A1 * | 9/2007 | Molnar et al. ............... | 604/503 |
| 2007/0233158 A1 | 10/2007 | Rodriguez | |

OTHER PUBLICATIONS

PCT Notification of Transmittal of the International Search Report and the Written Opinion of the International Searching Authority, or the Declaration dated Nov. 25, 2008.

* cited by examiner

*Primary Examiner* — Carl H Layno
*Assistant Examiner* — Allen Porter, Jr.
(74) *Attorney, Agent, or Firm* — Kenyon & Kenyon LLP

(57) ABSTRACT

A stimulation system can have a first sensor to generate a first reading and a second sensor to generate a second reading. An analysis module of a programmer such as a patient programmer, which programs a stimulation signal to be delivered to a patient, conducts an evaluation of the patient based on the first and second readings. Evaluations may include determinations such as range of motion determinations, posture determinations, physical task-specific brain activity determinations, cognitive task-specific brain activity determinations, and brain activity-specific movement determinations.

31 Claims, 3 Drawing Sheets

| Evaluation | | First Sensor | | Second Sensor | |
|---|---|---|---|---|---|
| No. | Description | ID | Type | ID | Type |
| 1 | Range of motion | $S_{PP1}$ | Accelerometer | $S_{IPG}$ | Accelerometer |
| 2 | Posture | $S_{BHC}$ | Accelerometer | $S_{IPG}$ | Accelerometer |
| 3 | Physical Task-specific $EEG_1$ | $S_{PP2}$ | Force | $S_{BHC}$ | EEG |
| 4 | Physical Task-specific $EEG_2$ | $S_{PP2}$ | Force | $S_{EXT}$ | EEG |
| 5 | Cognitive Task-specific EEG | $S_{PP3}$ | Keypad | $S_{EXT}$ | EEG |
| 6 | EEG-specific motion$_1$ | $S_{BHC}$ | EEG | $S_{IPG}$ | Accelerometer |
| 7 | EEG-specific motion$_2$ | $S_{BHC}$ | EEG | $S_{EXT}$ | Accelerometer |
| 8 | EEG-specific motion$_3$ | $S_{EXT}$ | EEG | $S_{IPG}$ | Accelerometer |
| 9 | EEG-specific motion$_4$ | $S_{EXT}$ | EEG | $S_{EXT}$ | Accelerometer |
| 10 | Coordinated muscular | $S_{PP1}$ | Accelerometer | $S_{PP2}$ | Force |
| ⋮ | | | | | |
| n | Lead migration | $S_{BHC}$ | Accelerometer | $S_{IPG}$ | Accelerometer |

DEEP BRAIN STIMULATION SYSTEM WITH INPUTS

BACKGROUND

1. Technical Field

This disclosure generally relates to the treatment and rehabilitation of patients having implanted medical devices. More particularly, the disclosure relates to the use of a distributed array of sensors to evaluate the progress of neuro-stimulation patients.

2. Discussion

Implantable neuro-stimulation systems have begun to demonstrate clinical usefulness for a wide variety of conditions such as spinal cord injury, traumatic brain injury (TBI), stroke, Parkinson's disease and Parkinson's tremor. For example, deep brain stimulation (DBS) systems have been used to successfully improve motor control in Parkinson's patients by delivering electrical pulses to selected areas of the brain. While certain developments in neuro-stimulation systems have advanced rehabilitation and treatment in a number of areas, certain challenges remain.

For example, most neuro-stimulation systems focus primarily on the delivery of the electrical pulses to the desired treatment site, with little or no ability to evaluate the progress of the patient. Systems that may have the ability to obtain information from the patient typically obtain data from a single source, and therefore may lack a system-level approach to patient evaluation. Accordingly, while there have been some advances in neuro-stimulation systems, there still remains considerable room for improvement.

BRIEF DESCRIPTION OF THE DRAWINGS

The various advantages of the embodiments of the present invention will become apparent to one skilled in the art by reading the following specification and appended claims, and by referencing the following drawings, in which:

DETAILED DESCRIPTION

Embodiments of the present invention provide for a stimulation system having a first sensor to generate a first reading and a second sensor to generate a second reading. The stimulation system may also include an analysis module of a stimulation system. The analysis module can conduct an evaluation of a patient based on the first reading and the second reading, wherein the patient receives a stimulation signal from the stimulation system. In one embodiment, the evaluation includes a determination of at least one of a range of motion of the patient, a posture of the patient, a task-specific brain activity of the patient, and a brain activity-specific movement of the patient.

In another embodiment of the invention, a deep brain stimulation (DBS) system includes an implantable pulse generator, which includes a first accelerometer to generate a first reading, wherein the implantable pulse generator generates a stimulation signal. The DBS system may include a stimulation extension to receive the stimulation signal from the implantable pulse generator and a brain stimulation lead to receive the stimulation signal from the stimulation extension and deliver the stimulation signal to a patient at a brain treatment site. A patient programmer, which may include a second accelerometer to generate a second reading, can compare the first reading to the second reading to obtain a relative measurement. The patient programmer may also determine a range of motion for the patient based on the relative measurement.

In yet another embodiment of the invention, a method of operating a stimulation system provides for transmitting a first reading from a first sensor to an analysis module of a stimulation system. A second reading may be transmitted from a second sensor to the analysis module, wherein the patient receives a stimulation signal from the stimulation system and an evaluation of the patient can be conducted based on the first reading and the second reading.

Figure 1:
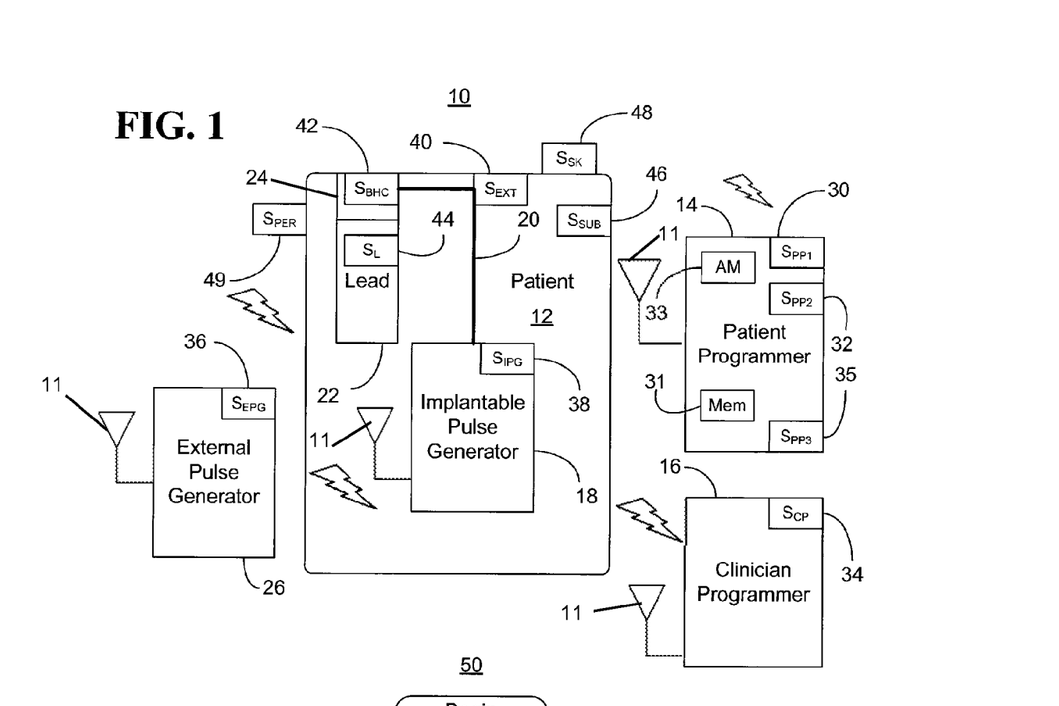
FIG. 1 is a block diagram of an example of a stimulation system according to an embodiment of the present invention.

FIG. 1 shows a stimulation system 10 that can generally be used to treat, rehabilitate, and evaluate a patient 12. In the illustrated example, the system 10 includes an array of sensors distributed across a patient programmer 14, which may be a relatively small handheld device, a clinician programmer 16, which typically runs as an application on a laptop- or PC-based platform, and a signal delivery arrangement having an implantable pulse generator 18, a stimulation extension 20, a stimulation lead 22 with a burr hole cap 24, and an optional external pulse generator 26. The implantable pulse generator (IPG) 18 may be used to deliver electrical pulses to areas of the patient's body such as, for example, the brain, spinal cord, or other parts of the nervous system, via the extension 20 and lead 22, which may also be implanted in the patient 12. For example, the IPG 18 may be implanted by placing the IPG 18 in a sub-cutaneous pocket created by making a blunt dissection in the subclavicular region, wherein the IPG 18 can include one or more suture holes for securing the IPG 18 to the muscle facia. In addition, the lead 22 may be tunneled to the distal end of the extension 20, and the extension 20 may be tunneled to the generator 18 using well-known implantation procedures. Thus, the illustrated IPG 18 generates stimulation signals, which are received by the stimulation extension 20 and transferred to the lead 22 for delivery to the patient 12 at the treatment site. The external pulse generator (EPG) 26 may also generate stimulation signals for delivery to the patient 12.

In this regard, the generators 18 and 26 may have a wide range of non-invasively programmable parameters and stimulation modes, and can exchange parameter information, via telemetry and communication interfaces 11, with the clinician programmer 16 and the patient programmer 14. The stimulation pulses delivered to the lead 22 can be determined by a parameter called a program, wherein a program can be a specific combination of amplitude, rate and pulse width parameters acting on a specific lead electrode set. For the stimulation signals, example amplitudes might range from 0.0-20.0 mA, example pulse widths may range from 10-1000 μsec per phase, example frequencies may range from 1-1200 Hz, and the waveform shape might be square, sine, or triangle wave. Other parameter ranges and characteristics may also be used.

As will be described in greater detail, the illustrated array of sensors can facilitate the treatment, rehabilitation and evaluation of the patient 12, so that the effectiveness of the stimulation signals is maximized. In particular, the patient programmer 14 can include a first patient programmer sensor ($S_{PP1}$) 30, a second patient programmer sensor ($S_{PP2}$) 32 and a third patient programmer sensor ($S_{PP3}$) 35, the clinician programmer 16 can include one or more clinician programmer sensors ($S_{CP}$) 34, and the EPG 26 can include one or more external pulse generator sensors ($S_{EPG}$) 36. In addition, the illustrated IPG 18 includes one or more IPG sensors ($S_{IPG}$) 38, the stimulation extension 20 includes one or more extension sensors ($S_{EXT}$) 40, the burr hole cap 24 includes one or more burr hole cap sensors ($S_{BHC}$) 42, and the lead includes one or more lead sensors ($S_L$) 44. The system 10 may also include a subcutaneous sensor ($S_{SUB}$) 46 implanted in the patient 12 and a skin sensor ($S_{SK}$) 48 coupled to the skin of the patient 12. Examples of the types of sensors that may be used include, but are not limited to, electroencephalogram (EEG) sensors, accelerometers, pressure sensors, temperature sensors, heart rate sensors and pH sensors. The sensors may also include input devices such as touch screens, microphones and keypads. The number, distribution, type and purpose of the sensors may vary depending upon the circumstances and treatment objectives. For example, one or more other peripheral sensors ($S_{PER}$) 49 such as saccadic eye movement goggles, accelerometer watches, and other devices may be used to provide input regarding the progress of the patient 12.

The sensors can generate time-stamped readings and transmit these readings to the programmers 14 and 16. The readings may be periodically generated, self-initiated or generated in response to a query from a programmer. The readings can also be transmitted wirelessly as appropriate. For example, the sensors that are in contact with the patient 12 may transmit their readings to the programmers 14 and 16 through a communication interface 11 in the IPG 18, wherein the communication interface 11 can be provided with short range wireless functionality such as WPAN (Wireless Personal Area Network; e.g., IEEE 802.15.4), Bluetooth (e.g., IEEE 802.15.1), WiFi (Wireless Fidelity; e.g., IEEE 802.11), or RF (Radio Frequency) with MICS (Medical Implant Communication Service; e.g., 47 CFR 95.601-95.673 Subpart E) functionality, or long range wireless functionality such as RF telemetry or WiMAX (Worldwide Interoperability for Microwave Access; e.g., IEEE 802.16) functionality. The EPG sensor 36 may transmit its readings to the programmers 14 and 16 using short range wireless, long range wireless, or wired communication such as a USB (Universal Serial Bus) or Ethernet (e.g., IEEE 802.3) communication, and the readings generated by the sensors coupled to the respective programmers 14 and 16 can be transferred between the programmers 14 and 16 using short range wireless, long range wireless, or wired communication. The illustrated patient programmer 14, which is typically much more accessible to the patient 12 than the clinician programmer 16 and tends to be much more "personal" to the patient 12, includes an analysis module (AM) 33 to conduct evaluations and a memory (Mem) 31 to store the various readings and evaluations to a memory 31 for later retrieval, reporting and/or analysis. The analysis module 33 and memory 31 may alternatively be disposed within the IPG 18, EPG 26 and/or clinician programmer 34.

Figure 2:
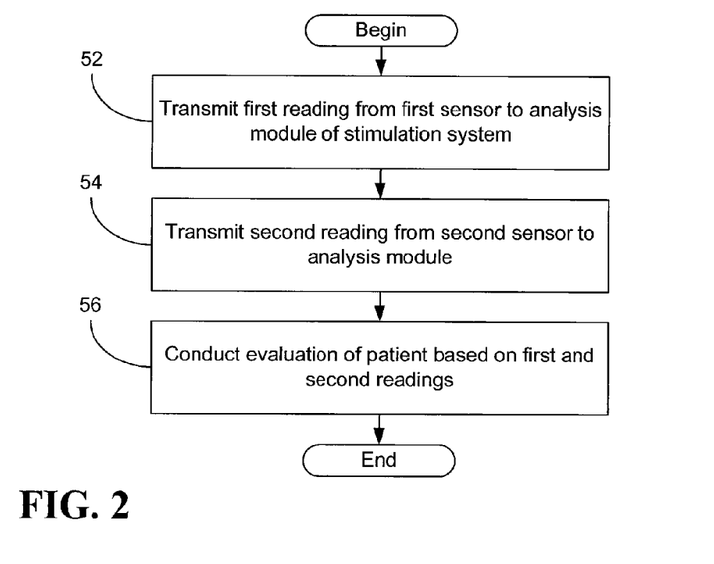
FIG. 2 is a flowchart of an example of a method of operating a stimulation system according to an embodiment of the present invention.

FIG. 2 shows a method 50 of operating a stimulation system. The method 50 may be implemented in a neuro-stimulation system as a set of processor-executable instructions stored in read only memory (ROM), random access memory (RAM), electrically erasable programmable ROM (EEPROM), flash memory, etc., as fixed functionality hardware such as an embedded microcontroller, application specific integrated circuit (ASIC), etc. using complementary metal oxide semiconductor (CMOS) technology or transistor-transistor-logic (TTL), or any combination thereof. Processing block 52 provides for transmitting a first reading from a first sensor to an analysis module of a stimulation system. A second reading is transmitted from a second sensor to the analysis module at block 54 and block 56 provides for conducting an evaluation of patient based on the first reading and the second reading, wherein the patient receives a stimulation signal from the stimulation system. Patient evaluations can involve determining the range of motion of the patient, posture of the patient, task-specific brain activity of the patient, brain activity-specific movement of the patient, and so on.

Figure 3:
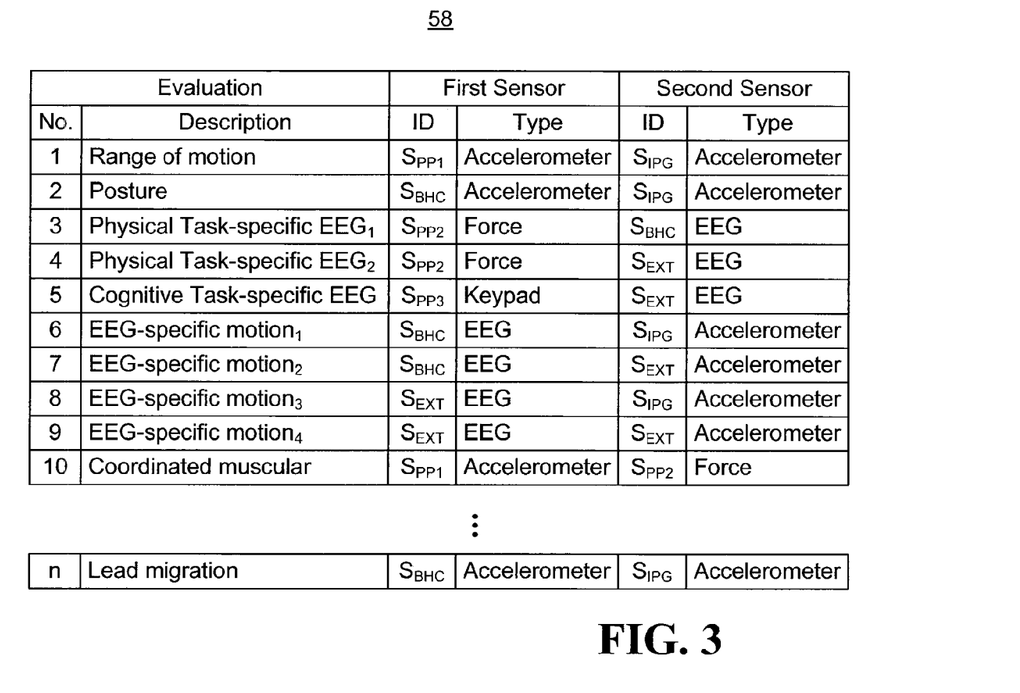
FIG. 3 is a diagram of an example of an evaluation table according to an embodiment of the present invention.

With continuing reference to FIGS. 1 and 3, an evaluation table 58 is shown, wherein the table 58 may be stored on and/or used by a programmer such as the patient programmer 14 to manage the collection of patient progress input and to conduct patient evaluations. The information in the table 58 may be organized in other formats such as relational databases, software routines, linked lists, etc. In particular, the table 58 may identify sensing parameters for "n" evaluations, wherein each evaluation provides insight into the patient's progress. For example, the illustrated Evaluation No. 1 involves determining the range of motion of the patient. In this evaluation, the patient can be instructed to lift the patient programmer 14 over his or her head, and readings can be obtained from the first patient programmer sensor 30 and the IPG sensor 38, wherein the sensors 30, 38 are accelerometers. The readings from the accelerometers, which may use a wide variety of technology such as piezoelectric, shear mode, surface micromachined capacitive, thermal, and capacitive spring mass based technology to measure their own motion, can be compared to determine the duration, relative speed, and distance of the motion, and therefore evaluate the range of motion of the patient.

The illustrated Evaluation No. 2 enables the programmer to assess the posture of the patient. In particular, accelerometer readings can be taken from the burr hole cap sensor 42 and the IPG sensor 38, wherein if the IPG sensor 38 is showing no motion and the burr hole cap sensor 42 is showing motion, the programmer can determine that the patient is sitting, lying down, or standing still while moving their head. The illustrated Evaluation Nos. 3-5 enable the programmer to determine task-specific brain activity levels. The tasks to be performed may be physical tasks or cognitive tasks. For example, the patient can be instructed to press on the second patient programmer sensor 32, which may be a standard pressure bar, to generate a force reading, while a simultaneous EEG signal is taken from a burr hole cap sensor for Evaluation No. 3 or an EEG signal is taken from the extension sensor 40 for Evaluation No. 4. In Evaluation No. 5, a cognitive question may be posed to the patient, wherein the patient's response to the question is obtained via the first reading from the third patient programmer sensor 35, which is a keypad in the illustrated example, and the patient's brain activity is obtained via the second reading. Other input devices, such as touch screens and microphones may also be used to obtain cognitive responses from the patient. In addition, cognitive input may be obtained by instructing the patient to press the pressure bar once for "no" and twice for "yes", for example.

The illustrated Evaluation Nos. 6-9 enable the programmer to determine brain activity-specific movement of the patient. In particular, the onset of a seizure or some other abnormal brain activity can be detected through the burr hole cap sensor 42 (Evaluation Nos. 6 and 7), or the extension sensor 40 (Evaluation Nos. 8 and 9), and accelerometer readings can be taken from the other sensors such as the IPG sensor 38 (Evaluation Nos. 6 and 8) or an extension sensor (Evaluation Nos. 7 and 9). Thus, the patient's movement during a seizure can be monitored and analyzed to identify potential correlations that can guide subsequent treatments.

Evaluation No. 10 provides for evaluating the patient's muscle group coordination by capturing accelerometer readings from the first patient programmer sensor 30 and force readings from the second patient programmer sensor 32. In this example, the patient could be instructed to lift the patient programmer 14 while squeezing the force sensor on the patient programmer 14. Thus, the accelerometer readings from the first patient programmer sensor 30 may provide information regarding the strength of the patient's arm muscles and the force readings from the second patient programmer sensor 32 may provide information regarding the strength of the patient's hand muscles. The evaluation can therefore use the readings from the two sensors to evaluate the extent to which the two muscle groups operate in conjunction with one another.

In yet another example, Evaluation No. n provides for detecting a migration of the stimulation lead 22 from the treatment site by comparing an accelerometer reading from the burr hole cap sensor 42 to an accelerometer reading from the IPG sensor 38. Thus, if the two readings indicate dissimilar motion, it can be determined that the lead 22 is becoming dislodged from the original treatment site. Alternatively, the two sensors could have the ability to interact with one another directly to determine relative motion. For example, an RF or other link could be established between the sensors, wherein signal strength or other position data may be used to establish a three-dimensional coordinate system and evaluate relative motion along one or more axes. As a result, the medical professional can be alerted and, as discussed in greater detail below, the stimulation signal may be adjusted accordingly. Other evaluations may be formulated using the distributed array of sensors to enhance the functionality of the stimulation system 10.

Figure 4:
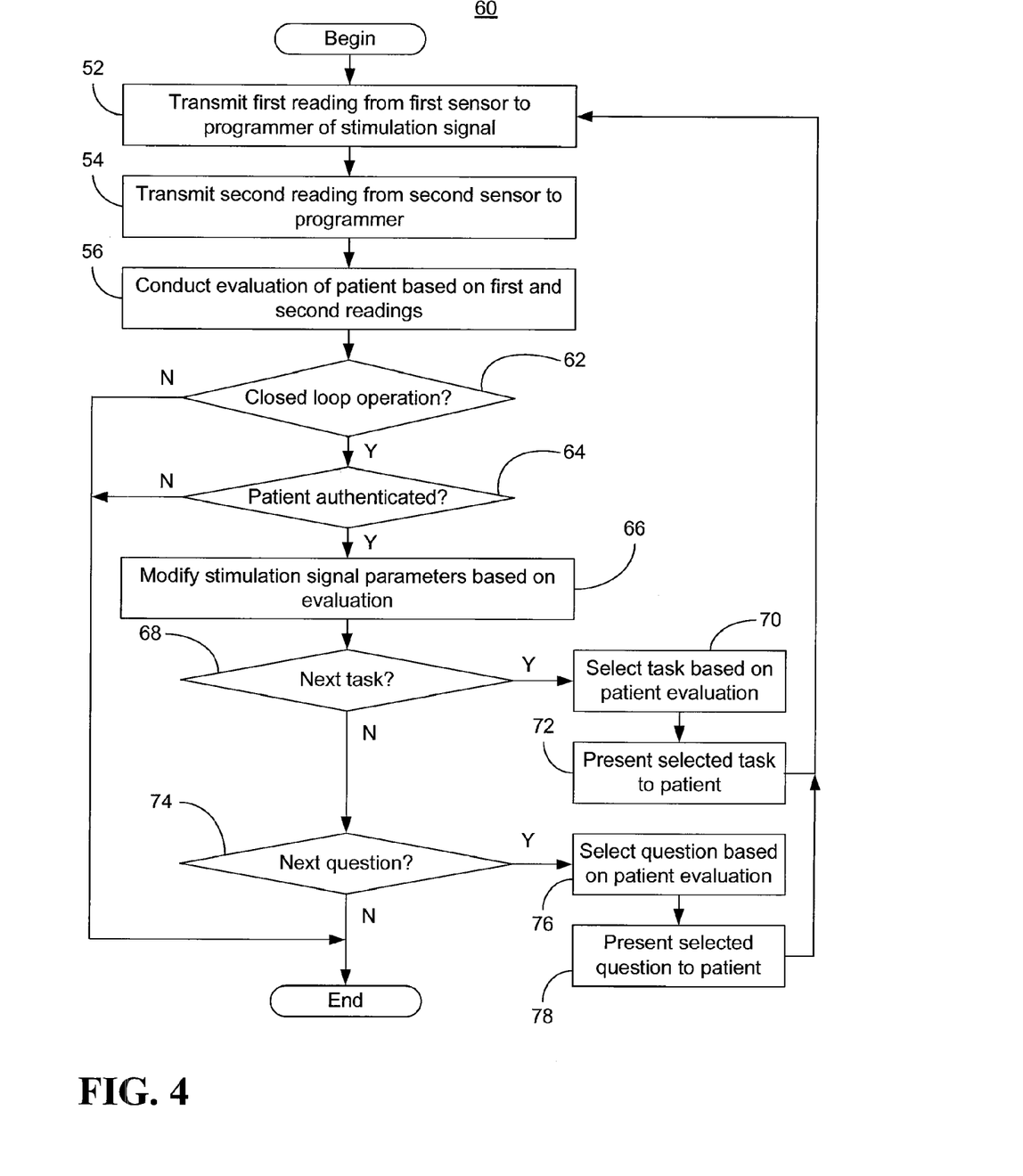
FIG. 4 is a flowchart of an example of a method of operating a closed loop stimulation system according to an embodiment of the present invention.

Turning now to FIG. 4, a method 60 of operating a closed loop stimulation system is shown. The method 60 may be implemented in a neuro-stimulation system as a set of processor-executable instructions stored in ROM, RAM, EEPROM, flash memory, etc., as fixed functionality hardware such as an embedded microcontroller, ASIC, etc. using CMOS technology or TTL, or any combination thereof. The illustrated example provides for transmission of readings to a programmer at blocks 52 and 54 and an evaluation at block 56 as already discussed, as well as certain additional closed loop functionality. In particular, block 62 provides for determining whether the stimulation system is to implement closed loop operation. Generally, closed loop operation can relate to the selection of stimulation signal parameters, the selection of instructions to present to the patient, the selection of questions to present to the patient, and so on. The determination at block 62 can be made by consulting a tamper-resistant flag that is set on the patient programmer by the medical professional during an office visit, for example.

If closed loop operation is enabled, block 64 provides for determining whether the client can be authenticated. The authentication, which can be facilitated by the use of a fingerprint identification pad, retina scanner, hair follicle analyzer, or other biometric authentication solution disposed on the patient programmer, enables verification that the individual performing tasks, answering questions, and/or otherwise using the patient programmer is in fact the patient. To further address safety concerns, the patient programmer may require the patient programmer and the pulse generator to be maintained in proximity to one another, as well as the maintenance of constant communication between the patient programmer and the pulse generator while patient progress input is being obtained. If the biometric data cannot be authenticated, the requisite proximity has not been maintained, or the requisite constant communication has not been maintained, the illustrated process exits out of closed loop operation.

If the patient is authenticated, block 66 provides for modification of one or more parameters of the stimulation signal based on the evaluation. For example, if it is determined from Evaluation No. 1 (FIG. 3) that the patient's range of motion has not been improving over time, block 66 may involve increasing the duty cycle of the stimulation signal pulses. In another example, if it is determined from Evaluation No. 3 (FIG. 3) that the patient exhibits unusually high levels of brain activity when pressing on the second patient programmer sensor 32 (FIG. 1), the programmer might reduce the amplitude of the stimulation signal pulses.

Block 68 provides for determining whether the patient is to be instructed to perform a task. Tasks may be related to specific evaluations, such as range of motion or task-specific EEG evaluations, or related to "diary" type entries. In this regard, the patient programmer may also provide instructions for tasks to be performed with other objects, wherein the patient and/or rehab technician may enter performance scores into the patient programmer. Table 1 below shows a plurality of Action Research Arm Test instructions/questions, which may be presented to the patient via a display or speaker of the patient programmer.

TABLE 1

| Action Research Arm Test Activity | Score |
|---|---|
| Grasp | |
| 1. Block, wood, 10 cm cube (If score = 3, total = 18 and go to Grip) Pick up a 10 cm block | |
| 2. Block, wood, 2.5 cm cube (If score = 0, total = 0 and go to Grip) Pick up 2.5 cm block | |
| 3. Block, wood, 5 cm cube | |
| 4. Block, wood, 7.5 cm cube | |
| 5. Ball (Cricket), 7.5 cm diameter | |
| 6. Stone 10 × 2.5 × 1 cm | |
| Coefficient of reproducibility = 0.98 | |
| Coefficient of scalability = 0.94 | |
| Grip | |
| 1. Pour water from glass to glass (If score = 3, total = 12, and go to Pinch) | |
| 2. Tube 2.25 cm (If score = 0, total = 0 and go to Pinch) | |
| 3. Tube 1 × 16 cm | |
| 4. Washer (3.5 cm diameter) over bolt | |
| Coefficient of reproducibility = 0.99 | |
| Coefficient of scalability = 0.98 | |
| Pinch | |
| 1. Ball bearing, 6 mm, $3^{rd}$ finger and thumb (If score = 3, total = 18 and go to Grossmt) | |
| 2. Marble, 1.5 cm, index finger and thumb (If score = 0, total = 0 and go to Grossmt) | |
| 3. Ball bearing $2^{nd}$ finger and thumb | |
| 4. Ball bearing $1^{st}$ finger and thumb | |
| 5. Marble $3^{rd}$ finger and thumb | |
| 6. Marble $2^{nd}$ finger and thumb | |
| Coefficient of reproducibility = 0.99 | |
| Coefficient of scalability = 0.98 | |
| Grossmt (Gross Movement) | |
| 1. Place hand behind head (If score = 3, total = 9 and finish) | |
| 2. (If score = 0, total = 0 and finish | |
| 3. Place hand on top of head | |
| 4. Hand to mouth | |
| Coefficient of reproducibility = 0.98 | |
| Coefficient of scalability = 0.97 | |

Thus, if it is determined at block 68 that the patient is to receive an instruction, block 70 provides for selecting the next task based on a previous patient evaluation. For example, if it is determined from Evaluation No. 4 (FIG. 3) that pressing on the second patient programmer sensor 32 (FIG. 1) does not result in a significant increase in brain activity, block 70 may decide to instruct the patient to perform the range of motion task associated with Evaluation No. 1 (FIG. 3). In another example, if it is determined from Evaluation No. n that the lead is migrating from the original treatment site, block 70 might result in a decision to instruct the patient to perform the task-specific EEG task associated with Evaluation No. 3 (FIG. 3). The selected instructions are presented to the patient at block 72.

If the patient is not to receive another instruction, block 74 provides for determining whether a question should be presented to the patient. In this regard, the display and/or speaker of the patient programmer may also be used to present questions to the patient that are tailored to the patient's progress, wherein the patient can provide answers to the questions via buttons or other input devices on the patient programmer. The progress input questions could be related to the patient's perception of improvement, the patient's psychological state, objective yes/no issues, or anything else related to the patient's well-being or state of recovery. In general, questions may be related to quality of life (e.g., physical, emotional, task oriented), object recognition (e.g., display an apple, plane, basketball, etc., and have the patient choose from a multiple choice list what the object is), diary input (e.g., time/date stamp for eating, bathing, voiding), and cognitive state (e.g., IQ).

For example, Table 2 shows a plurality of Barthel Index questions, which may be selected at block 76 based on the patient evaluation.

TABLE 2

| Barthel Index Activity | Score |
| --- | --- |
| FEEDING | |
| 0 = unable | |
| 5 = needs help cutting, spreading butter, etc., or requires modified diet | |
| 10 = independent | |
| BATHING | |
| 0 = dependent | |
| 5 = independent (or in shower) | |
| GROOMING | |
| 0 = needs to help with personal care | |
| 5 = independent face/hair/teeth/shaving (implements provided) | |
| DRESSING | |
| 0 = dependent | |
| 5 = needs help but can do about half unaided | |
| 10 = independent (including buttons, zips, laces, etc.) | |
| BOWELS | |
| 0 = incontinent (or needs to be given enemas) | |
| 5 = occasional accident | |
| 10 = continent | |
| BLADDER | |
| 0 = incontinent, or catheterized and unable to manage alone | |
| 5 = occasional accident | |
| 10 = continent | |
| TOILET USE | |
| 0 = dependent | |
| 5 = needs some help, but can do something alone | |
| 10 = independent (on and off, dressing, wiping) | |
| TRANSFERS (BED TO CHAIR AND BACK) | |
| 0 = unable, no sitting balance | |
| 5 = major help (one or two people, physical), can sit | |
| 10 = minor help (verbal or physical) | |

TABLE 2-continued

| Barthel Index Activity | Score |
| --- | --- |
| 15 = independent | |
| MOBILITY (ON LEVEL SURFACES) | |
| 0 = immobile or <50 yards | |
| 5 = wheelchair independent, including corners, >50 yards | |
| 10 = walks with help of one person (verbal or physical) >50 yards | |
| 15 = independent (but may use any aid; for example, stick) >50 yards | |
| STAIRS | |
| 0 = unable | |
| 5 = needs help (verbal, physical, carrying aid) | |
| 10 = independent | |

Table 3 shows a plurality of Short Form 36 (SF-36) Health Survey questions, which may be selected at block 76 based on the patient evaluation.

TABLE 3

| SF-36 Health Survey Question |
| --- |
| 1. In general, would you say your health is: |
| __ Excellent |
| __ Very Good |
| __ Good |
| __ Fair |
| __ Poor |
| 2. Compared to one year ago, how would you rate your health in general now? |
| __ Much better now than a year ago |
| __ Somewhat better now than a year ago |
| __ About the same as one year ago |
| __ Somewhat worse now than one year ago |
| __ Much worse now than one year ago |
| . |
| . |
| . |
| 11. How TRUE or FALSE is each of the following statements for you? |
| a. I seem to get sick a little easier than other people |
| __ Definitely true |
| __ Mostly true |
| __ Don't know |
| __ Mostly false |
| __ Definitely false |
| b. I am as healthy as anybody I know |
| __ Definitely true |
| __ Mostly true |
| __ Don't know |
| __ Mostly false |
| __ Definitely false |
| c. I expect my health to get worse |
| __ Definitely true |
| __ Mostly true |
| __ Don't know |
| __ Mostly false |
| __ Definitely false |
| d. My health is excellent |
| __ Definitely true |
| __ Mostly True |
| __ Don't know |
| __ Mostly false |
| __ Definitely false |

Table 4 shows a plurality of Stroke Specific Quality of Life Scale (SS-QOL) questions, which may be selected at block 76 based on the patient evaluation.

TABLE 4

Copyright © 1997-2007 - Internet Stroke Center

| SS-QOL Item | Score |
|---|---|
| Energy | |
| 1. I felt tired most of the time. | |
| 2. I had to stop and rest during the day. | |
| 3. I was too tired to do what I wanted to do. | |
| Family Roles | |
| 1. I didn't join in activities just for fun with my family. | |
| 2. I felt I was a burden to my family. | |
| 3. My physical condition interfered with my personal life. | |
| Language | |
| 1. Did you have trouble speaking? For example, get stuck, stutter, stammer, or slur your words? | |
| 2. Did you have trouble speaking clearly enough to use the telephone? | |
| 3. Did other people have trouble in understanding what you said? | |
| 4. Did you have trouble finding the word you wanted to say? | |
| 5. Did you have to repeat yourself so others could understand you? | |
| . | |
| . | |
| . | |
| Work Productivity | |
| 1. Did you have trouble doing daily work around the house? | |
| 2. Did you have trouble finishing jobs that you started? | |
| 3. Did you have trouble doing the work you used to do? | |

As already noted, the selection of such progress input questions can be made based on the readings obtained from the various sensors and/or the resulting evaluations. For example, if it has been determined that the patient is sitting, lying down, or standing still while moving their head (Evaluation No. 2), the patient programmer could decide to ask the patient IQ-type questions to determine whether this type of posture has an impact on their cognitive state. In another example, if it has been determined that the stimulation lead has been migrating from the intended treatment site (Evaluation No. n), the patient programmer might decide to ask the patient questions relating to his or her physical and/or emotional well being to determine whether such migration has had an impact on their quality of life. The selected question is presented to the patient at block 78.

The present invention also provides methods of monitoring the progress of a patient who has been treated with neuromodulation using a patient programmer as described herein. Such a patient programmer can be used to monitor the progress of various different types of patients including those receiving neuromodulation for treatment of stroke, traumatic brain injury, or other conditions.

The terms "connected", "coupled" and "attached" are used herein to refer to any type of relationship, direct or indirect, between the components in question, and may apply to electrical, mechanical, RF, optical or other couplings, unless otherwise indicated. In addition, the term "first", "second", and so on are used herein only to facilitate discussion, and do not necessarily infer any type of temporal or chronological relationship.

Those skilled in the art will appreciate from the foregoing description that the broad techniques of the embodiments of the present invention can be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specifications, and following claims.

What is claimed is:

1. A deep brain stimulation system for determining the effectiveness of the treatment of a patient comprising:
   an implantable pulse generator configured to generate a stimulation signal;
   a brain stimulation lead configured to receive the stimulation signal from the implantable pulse generator and configured to deliver the stimulation signal to a patient at a brain treatment site; and
   at least one of a clinician programmer or a patient programmer configured to exchange information with the implantable pulse generator, wherein one of the clinician programmer or the patient programmer comprises a first sensor that generates a first reading and the implantable pulse generator or the brain stimulation lead comprises a second sensor that generates a second reading,
   wherein one of the clinician programmer, the patient programmer, or the implantable pulse generator comprises a processor configured to compare the first reading to the second reading to obtain a relative measurement of motion or posture and to evaluate the patient based on the relative measurement of motion or posture, and
   wherein the system further comprises communication interfaces for transmitting the first and second readings to the processor from the implantable pulse generator, the brain stimulation lead, the clinician programmer and the patient programmer via a wireless connection or a wired connection.

2. The deep brain stimulation system of claim 1, further comprising a display, wherein the processor is further configured to select a progress input question for presentation to the patient via the display based on the relative measurement.

3. The deep brain stimulation system of claim 1, further comprising a display, wherein the processor is further configured to select a task instruction for presentation to the patient via the display based on the relative measurement.

4. The deep brain stimulation system of claim 1, wherein the processor is further configured to select a set of parameters for the stimulation signal and modify at least one parameter in the set of parameters based on the relative measurement.

5. The deep brain stimulation system of claim 1, wherein the evaluation includes a determination of at least one of a range of motion of the patient, or a posture of the patient.

6. The deep brain stimulation system of claim 1, wherein the deep brain stimulation system is further configured to modify a parameter of the stimulation signal based on the evaluation.

7. The deep brain stimulation system of claim 1, further comprising a display, wherein the deep brain stimulation system is further configured to select at least one of a progress input question and a task instruction for presentation to the patient via the display based on the evaluation.

8. The deep brain stimulation system of claim 1, wherein one of the clinician programmer, the patient programmer, or the implantable pulse generator further comprises a memory configured to store data from the processor relating to the evaluation.

9. The deep brain stimulation system of claim 1, further comprising a third sensor to generate a third reading, wherein the third reading is configured to be transmitted to the processor via a wireless or wired connection to conduct the evaluation of the patient based on the third reading.

10. The deep brain stimulation system of claim 9, wherein the third sensor is selected from a group consisting of electroencephalogram sensors, accelerometers, pressure sensors, temperature sensors, heart rate sensors, pH sensors, touch screens, microphones and keypads.

11. The deep brain stimulation system of claim 9, wherein the third sensor is saccadic eye movement goggles.

12. The deep brain stimulation system of claim 1, wherein the first sensor is in the patient programmer, and the second sensor is in the implantable pulse generator.

13. The deep brain stimulation system of claim 12, wherein the processor is configured to receive, via a communication interface associated with the first sensor, the second sensor, and the processor, first and second readings from the first and second sensors, respectively, and the processor is further configured to obtain a relative measurement of a range of motion of the patient based on the comparison of the first and second readings.

14. The deep brain stimulation system of claim 1, wherein the first sensor is an accelerometer and the second sensor is an accelerometer.

15. The deep brain stimulation system of claim 14, wherein the processor is configured to receive, via a communication interface associated with the first accelerometer, the second accelerometer, and the processor, first and second readings from the first and second accelerometers, respectively, and the processor is further configured to obtain a relative measurement of the posture of the patient.

16. A deep brain stimulation system for determining the effectiveness of the treatment of a patient comprising:
   an implantable pulse generator adapted to generate a stimulation signal;
   a brain stimulation lead adapted to receive the stimulation signal from the implantable pulse generator and adapted to deliver the stimulation signal to a patient at a brain treatment site;
   a burr hole cap; and
   at least one of a clinician programmer or a patient programmer to exchange information with the implantable pulse generator,
   wherein the patient programmer comprises a first accelerometer that generates a first reading,
   wherein the implantable pulse generator, the brain stimulation lead, or the clinician programmer comprises a second accelerometer that generates a second reading,
   wherein one of the clinician programmer, the patient programmer, or the implantable pulse generator comprises a processor configured to compare the first reading to the second reading to obtain a relative measurement of motion or posture and to evaluate the patient based on the relative measurement of motion or posture,
   wherein the system further comprises communication interfaces for transmitting the first and second readings to the processor from the implantable pulse generator, the brain stimulation lead, the clinician programmer and the patient programmer via a wireless connection or a wired connection, and
   wherein the burr hole cap comprises a third accelerometer to generate a third reading, the processor further configured to detect a migration of the stimulation lead from the brain treatment site based on the third reading.

17. A deep brain stimulation system for determining the effectiveness of the treatment of a patient comprising:
   an implantable pulse generator adapted to generate a stimulation signal;
   a brain stimulation lead adapted to receive the stimulation signal from the implantable pulse generator and adapted to deliver the stimulation signal to a patient at a brain treatment site;
   a programmer adapted to be external to the patient, wherein the programmer comprises an accelerometer that generates a first reading and a pressure sensor that generates a second reading, wherein the second reading is a force reading,
   wherein the programmer, or the implantable pulse generator comprises a processor configured to receive, via a communication interface associated with the accelerometer, the pressure sensor, and the processor, first and second readings from the accelerometer and the pressure sensor, respectively, and the processor is further configured to compare the first reading to the second reading to evaluate the patient's muscle group coordination.

18. A deep brain stimulation system for determining the effectiveness of the treatment of a patient comprising:
   a first sensor, adapted to be attached to or contained within the patient, configured to generate a first reading;
   an implantable pulse generator configured to generate a stimulation signal;
   a brain stimulation lead configured to receive the stimulation signal from the implantable pulse generator and configured to deliver the stimulation signal to a patient at a brain treatment site; and
   at least one of a clinician programmer or a patient programmer configured to exchange information with the implantable pulse generator, wherein one of the clinician programmer or the patient programmer comprises a second sensor that generates a second reading,
   wherein one of the clinician programmer, the patient programmer, or the implantable pulse generator comprises a processor configured to compare the first reading to the second reading to obtain a relative measurement of motion or posture and to evaluate the patient based on the relative measurement of motion or posture, and
   wherein the system further comprises communication interfaces configured to transmit the first and second readings to the processor from the implantable pulse generator, the brain stimulation lead, the clinician programmer and the patient programmer via a wireless connection or a wired connection.

19. The deep brain stimulation system of claim 18, further comprising a display, wherein the processor is further configured to select a progress input question for presentation to the patient via the display based on the relative measurement.

20. The deep brain stimulation system of claim 18, further comprising a display, wherein the processor is further configured to select a task instruction for presentation to the patient via the display based on the relative measurement.

21. The deep brain stimulation system of claim 18, wherein the processor is further configured to select a set of parameters for the stimulation signal and modify at least one parameter in the set of parameters based on the relative measurement.

22. The deep brain stimulation system of claim 18, wherein the evaluation includes a determination of at least one of a range of motion of the patient, or a posture of the patient.

23. The deep brain stimulation system of claim 18, wherein the deep brain stimulation system is further configured to modify a parameter of the stimulation signal based on the evaluation.

24. The deep brain stimulation system of claim 18, further comprising a display, wherein the deep brain stimulation system is further configured to select at least one of a progress input question and a task instruction for presentation to the patient via the display based on the evaluation.

25. The deep brain stimulation system of claim 18, further including a third sensor to generate a third reading, wherein the third reading is configured to be transmitted to the processor via a wireless or wired connection to conduct the evaluation of the patient based on the third reading.

26. The deep brain stimulation system of claim 25, wherein the third sensor is selected from a group consisting of electroencephalogram sensors, accelerometers, pressure sensors, temperature sensors, heart rate sensors, pH sensors, touch screens, microphones and keypads.

27. The deep brain stimulation system of claim 18, wherein one of the clinician programmer, the patient programmer, or the implantable pulse generator further comprises a memory configured to store data from the processor relating to the evaluation.

28. The deep brain stimulation system of claim 18, wherein the third sensor is saccadic eye movement goggles.

29. The deep brain stimulation system of claim 18, wherein the processor is configured to receive, via a communication interface associated with the first sensor, the second sensor, and the processor, first and second readings from the first and second sensors, respectively, and the processor is further configured to obtain a relative measurement of a range of motion of the patient based on the comparison of the first and second readings.

30. The deep brain stimulation system of claim 18, wherein the first sensor is an accelerometer and the second sensor is an accelerometer.

31. The deep brain stimulation system of claim 30, wherein the processor is configured to receive, via a communication interface associated with the first accelerometer, the second accelerometer, and the processor, first and second readings from the first and second accelerometers, respectively, and the processor is further configured to obtain a relative measurement of the posture of the patient.

* * * * *